US00PP34422P2

(12) United States Plant Patent
Bruinen

(10) Patent No.: US PP34,422 P2
(45) Date of Patent: Jul. 12, 2022

(54) ***ZAMIOCULCAS* PLANT NAMED 'EDZAM1901'**

(50) Latin Name: ***Zamioculcas zamiifolia* (hort. Lodd.) Engl.**
Varietal Denomination: 'EDZAM1901'

(71) Applicant: Ed Holding B.V., Maasdijk (NL)

(72) Inventor: Ed Bruinen, Maasdijk (NL)

(73) Assignee: Ed Holding B.V., Maasdijk (NL)

( * ) Notice: Subject to any disclaimer, the term of this patent is extended or adjusted under 35 U.S.C. 154(b) by 0 days.

(21) Appl. No.: 17/300,789

(22) Filed: Nov. 9, 2021

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
See application file for complete search history.

(56) References Cited

PUBLICATIONS

Community Plant Variety Office (CPVO) Register—CPVO Application Consultation—for cultivar 'EDZAM1901'. Retrieved from the Internet on Jan. 11, 2021. (3 pages total).*

* cited by examiner

*Primary Examiner* — Susan McCormick Ewoldt
(74) *Attorney, Agent, or Firm* — Samuel R. McCoy, Jr.

(57) ABSTRACT

'EDZAM1901' is a new and distinctive *Zamioculcas* plant which is characterized by a very upright growth habit, with leaves comprised of large narrowly obovate to oblanceolate leaflets born on yellow-green petioles that are suffused and blotched brown. The new plant propagates successfully by leaf cuttings and has shown to be uniform and stable in the resulting generations from asexual propagation.

3 Drawing Sheets

Latin name of the genus and species: The Latin name of the genus and species of the novel variety disclosed herein is *Zamioculcas zamiifolia* (hort. Lodd.) Engl.

Variety denomination: The inventive variety of *Zamioculcas* disclosed herein has been given the variety denomination 'EDZAM1901'.

BACKGROUND OF THE INVENTION

Parentage: 'EDZAM1901' is a seedling selection resulting from the controlled pollination of a *Zamioculcas zamiifolia* 'E', the seed parent, with *Zamioculcas zamiifolia* 'U', the pollen parent, at a commercial nursery in Maasdijk, The Netherlands, in the summer of 2017. Both parents were developed and are owned by the inventor and were never released or patented. In the summer of 2017, one plant was observed to exhibit unique growth characteristics and was isolated for further evaluation in order to confirm the distinctness and stability of the characteristics first observed. Upon confirmation of distinctness and stability, 'EDZAM1901' was selected for commercialization.

Asexual Reproduction: Asexual reproduction of 'EDZAM1901' was first accomplished in 2017 by way of stem cuttings at a commercial greenhouse in Maasdijk, The Netherlands. Four successive generations produced from stem cuttings have shown that the unique features of the instant cultivar are stable and reproduce true to type.

SUMMARY OF THE INVENTION

The cultivar 'EDZAM1901' has not been observed under all possible environmental conditions and the phenotype may vary somewhat with variations in the instant environment such as temperature, day length, and light intensity, without, however, any variance in genotype. The following characteristics have been repeatedly observed and represent the distinguishing characteristics of the new *Zamioculcas* plant, 'EDZAM1901'. These traits, in combination, distinguish 'EDZAM1901' as a new and distinct cultivar.

1. *Zamioculcas* 'EDZAM1901' exhibits a very upright growth habit; and
2. *Zamioculcas* 'EDZAM1901' exhibits large, narrowly obovate to oblanceolate foliage; and
3. *Zamioculcas* 'EDZAM1901' exhibits medium green leaflets borne yellow-green petioles that are suffused and blotched brown.

BOTANICAL DESCRIPTION OF THE PLANT

Figure 1:
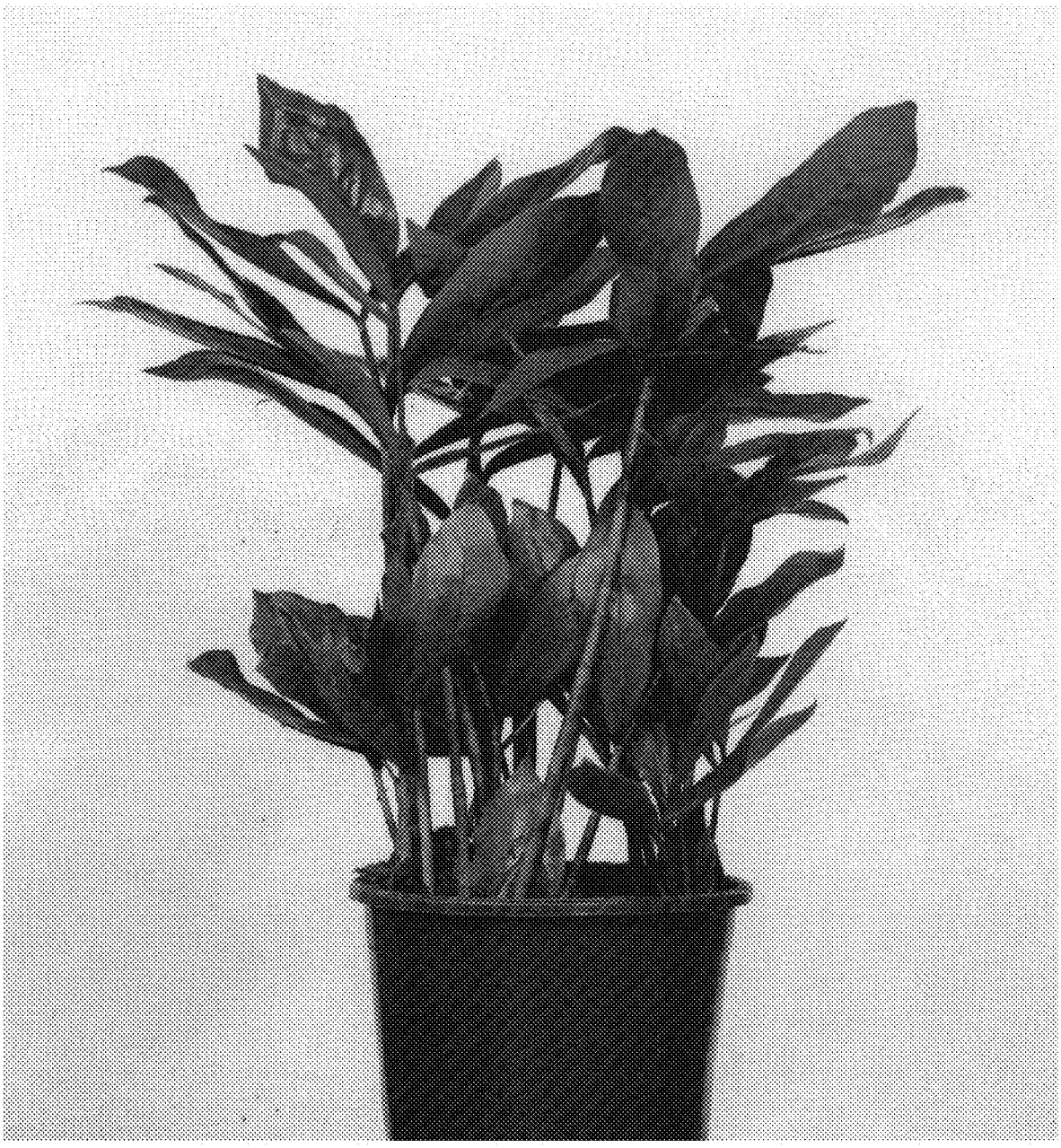
FIG. 1 shows, as nearly true as it is reasonably possible to make the same in color illustrations of this type, the typical foliage and growth characteristics of the new cultivar, 'EDZAM1901'. The plant shown is approximately 12 months old, potted into a 15 cm nursery pot, grown at a commercial greenhouse in Maasdijk, The Netherlands.
Figure 2:
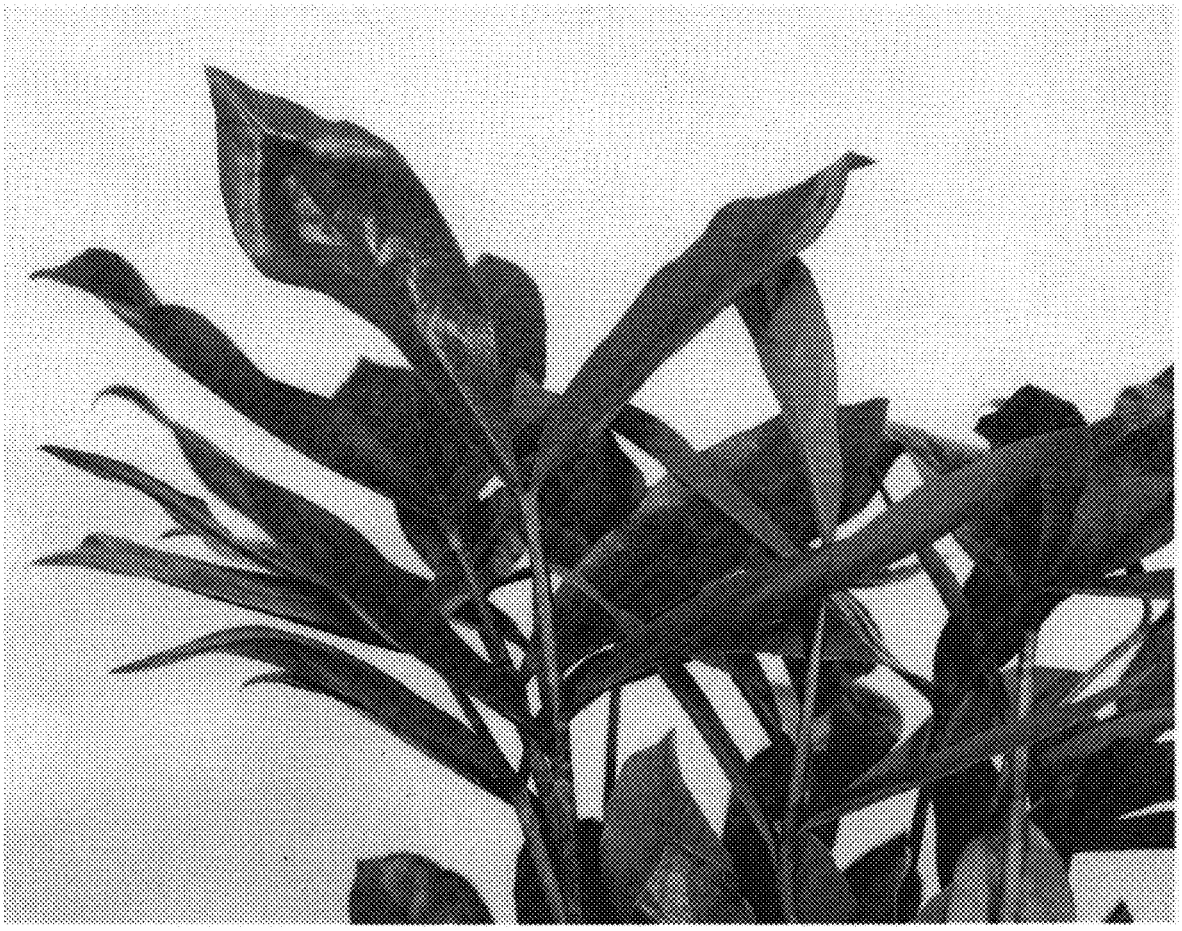
FIG. 2 shows, as nearly true as it is reasonably possible to make the same in color illustrations of this type, the typical foliage of the plant in FIG. 1.
Figure 3:
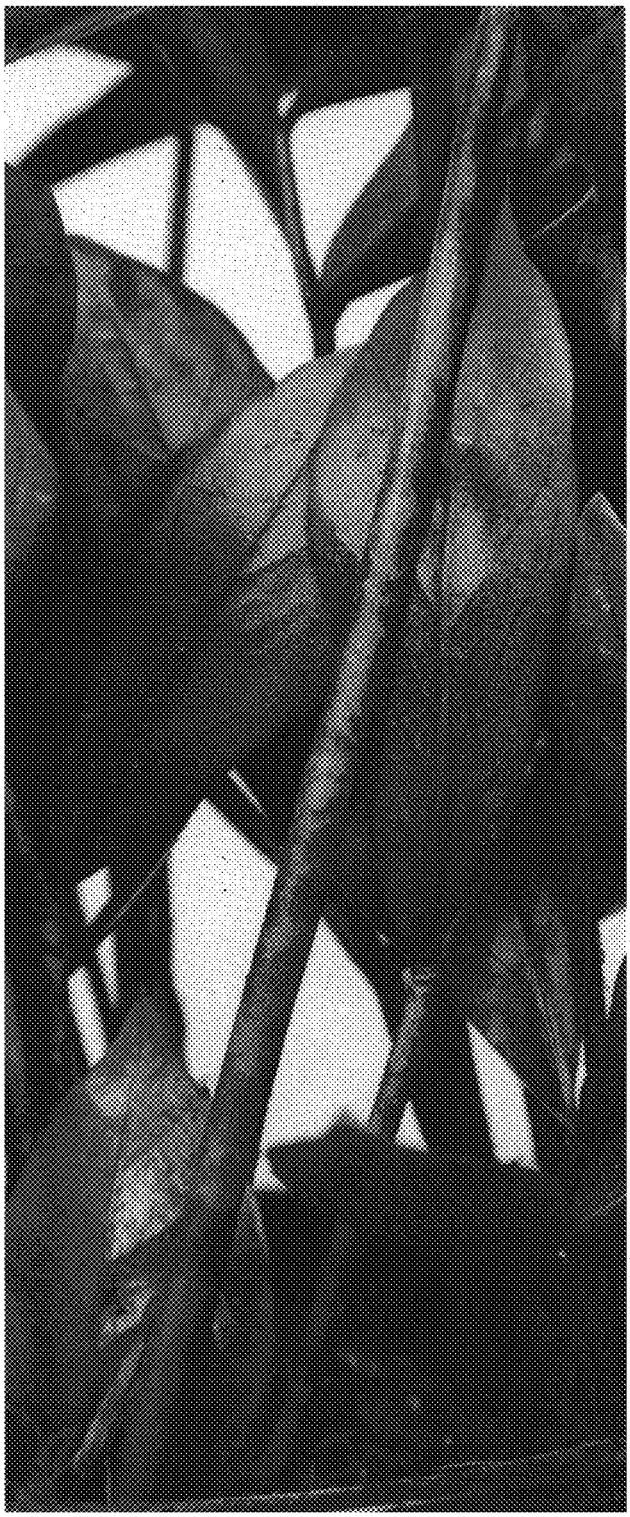
FIG. 3 shows, as nearly true as it is reasonably possible to make the same in color illustrations of this type, the typical petiole of the plant in FIG. 1.

The following is a detailed botanical description of a new and distinct variety of *Zamioculcas zamiifolia* known as 'EDZAM1901', based upon observations of 12-month-old plants, potted into 15 cm nursery pots and grown indoors at a commercial greenhouse in Maasdijk, The Netherlands. Plants were grown in full sun using accepted fertility and irrigation practices for *Zamioculcas* plants including overhead irrigation, fertilizer applications as needed, and supplemental Calcium treatments. With the exception of preventative fungicides, no chemical pest control measures were employed. Furthermore, no artificial light or photoperiodic treatments were given to the plants. Observation data was recorded in March of 2021.

Those skilled in the art will appreciate that certain characteristics will vary with older or, conversely, with younger plants. 'EDZAM1901' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, sixth edition, 2015.

A botanical description of 'EDZAM1901' and comparisons with the parent plants and the most similar variety of common knowledge are provided below.

General plant description:

*Growth habit*.—Tropical evergreen perennial.

*Plant profile shape*.—Broad oblong.

*Growth rate*.—Moderately fast growing.

*Plant vigor*.—Moderately vigorous.

*Height*.—38.5 cm to the top of the foliar plane.

*Width*.—35.8 cm.

*Propagation*.—Type — Leaf cuttings. Time to initiate rooting — Approximately 30 days at an approximate temperature of 25 degrees Celsius. Crop time — Approximately 1 year to produce a marketable plant in a 12 cm container.

*Pathogen and pest resistance and susceptibility*.—Plants have not been observed to be susceptible or resistant to pathogens and pests common to *Zamioculcas* sp.

*Environmental tolerances*.—Adapt to, at least, USDA Zones 10 to 12 and temperatures ranging from 5 to 40 degrees Celsius; moderate tolerance to rain; low tolerance to wind.

Stem:

*Branching habit*.—No stems or branches; compound leaves in small clumps, arising directly from tuberous rhizomes.

*Number of clumps per plant*.—6, on average.

*Number of additional clumps formed each year*.—6, on average.

Root system:

*Type*.—Tuberous rhizomes bearing thick fleshy roots.

*Shape of rhizomes*.—Irregular broad oblong to ovoid.

*Dimensions of rhizomes*.—2.2 cm long and 1.8 cm in diameter.

*Density of rhizomes and roots*.—Moderately dense.

*Distribution of rhizomes and roots*.—Rhizomes shallow; roots distributed evenly throughout the soil profile, from shallow to deep.

*Texture of rhizomes and roots*.—Glabrous and very fleshy.

*Color of rhizomes and roots*.—Greyed-green, nearest to a mixture of RHS 195A, 195B, and 195C.

Foliage:

*Arrangement*.—Compound leaves in small clumps, arising directly from tuberous rhizomes.

*Attachment*.—Petiolate.

*Division*.—Pinnately compound.

*Leaf profile shape*.—Broad ovate.

*Dimensions*.—37.2 cm long and 24.3 cm wide.

*Attitude*.—Upright; approximately 20 degrees from vertical.

*Quantity*.—Approximately 4 leaves per clump.

*Stipules*.—General — A leafy stipule is present at the base of each pinnately compound leaf. Shape — Lanceolate. Length — 8.1 cm. Width — 1.5 cm. Apex — Acute. Base — Broad cuneate. Margin — Entire, moderately undulated. Texture — Papery. Color, adaxial and abaxial surfaces — Translucent greyed-brown, nearest to RHS 199C.

*Petiole*.—Aspect — Elliptic; thickened at the base. Length — 10.0 cm; 27.5 cm, including all rachises. Diameter — 0.9 cm at the base; 0.8 cm below the first leaflet. Strength — Strong. Texture — Smooth and glabrous. Luster — Matte. Color, adaxial surface — Yellow-green, nearest to RHS 147B, and heavily suffused and blotched with brown, nearest to RHS 200A. Color, abaxial surface — Yellow-green, nearest to in between RHS 147B and 147C, and lightly suffused and blotched with brown, nearest to a mixture of RHS 200A and 200B.

*Rachis*.—Aspect — Rounded; tapering slightly from the proximal end to the apex. Length — 17.5 cm. Diameter — 0.55 cm. Strength — Strong. Texture — Smooth and glabrous. Luster — Matte. Color, adaxial surface — Nearest to a mixture of yellow-green and greyed-green, RHS 147D and 194B; heavily blotched and suffused with brown, nearest to a mixture of RHS 200A and N200A. Color, abaxial surface — Nearest to a mixture of yellow-green and greyed-green, RHS 147D and 194B; heavily blotched and suffused with brown, nearest to a mixture of RHS 200A and N200A.

*Leaflets*.—Quantity — Typically 4 leaflets. Attitude — At an angle of approximately 65 degrees to the rachis. Dimensions — 13.9 cm long and 4.8 cm wide. Shape — Narrow obovate to oblanceolate. Aspect — Slightly carinate and lightly curled inward. Apex — Acute to short apiculate. Base — Attenuate. Margin — Entire; slight, coarse undulation. Texture, adaxial surface — Glabrous and moderately coriaceous. Texture, abaxial surface — Glabrous and moderately coriaceous. Luster, adaxial surface — Glossy. Luster, abaxial surface — Glossy. Color — Juvenile foliage color, adaxial surface — Green, nearest to RHS 137A, and suffused with a darker shade of green, nearest to RHS 143A yet darker and more intense. Juvenile foliage color, abaxial surface — Nearest to in between green and yellow-green, RHS 143A and 144A. Mature leaf color, adaxial surface — Green, nearest to in between RHS NN137A and 139A yet darker and more intense. Mature leaf color, abaxial surface — Yellow-green, nearest to in between RHS 144A and 146A yet more intense. Venation — Pattern — Pinnate. Vein color, adaxial surface — Green, nearest to RHS 143B. Vein color, abaxial surface — Yellow-green, nearest to RHS 144A, and suffused with brown towards the base, nearest to RHS N200A. Petiolule — Aspect — Flattened oval. Length — 0.5 cm. Diameter — Petiolule flattened; average width is 0.4 cm and the average height is 0.35 cm. Strength — Strong. Texture, adaxial and abaxial surfaces — Smooth and glabrous. Luster, adaxial and abaxial surfaces — Matte. Color, adaxial surface — Yellow-green, nearest to RHS 146A, and suffused with brown, nearest to RHS N200A. Color, abaxial surface — Yellow-green, nearest to RHS 147A, and suffused with brown, nearest to RHS N200A.

Inflorescence: No flowering has been observed to date.

COMPARISON WITH THE PARENT PLANTS

Plants of the new cultivar 'EDZAM1901' may be distinguished from its seed parent, *Zamioculcas zamiifolia* 'E', by the characteristics described in Table 1.

TABLE 1

Comparison Between 'EDZAM1901' and The Seed Parent

| Characteristic | 'EDZAM1901' | The Seed Parent |
|---|---|---|
| Abundance of foliage. | More abundant. | Less abundant. |
| Leaflet apex. | More acute. | More rounded. |
| General coloration of the foliage. | Darker shade of green compared to the parent. | Lighter shade of green compared to 'EDZAM1901'. |

Plants of the new cultivar 'EDZAM1901' may be distinguished from its pollen parent, *Zamioculcas zamiifolia* 'U', by the characteristics described in Table 2.

TABLE 2

Comparison Between 'EDZAM1901' and The Pollen Parent

| Characteristic | 'EDZAM1901' | The Pollen Parent |
|---|---|---|
| Abundance of foliage. | Less abundant. | More abundant. |
| Leaflet apex. | More rounded. | More acute. |
| General coloration of the foliage. | Lighter shade of green compared to the parent. | Darker shade of green compared to 'EDZAM1901'. |

COMPARISONS WITH THE MOST SIMILAR VARIETY OF COMMON KNOWLEDGE

Plants of the new cultivar 'EDZAM1901' are most similar to the commercial variety, *Zamioculcas* 'EDZAM1702' (U.S. Plant Pat. No. 33,429). A comparison of 'EDZAM1901' with 'EDZAM1702' is described in Table 3.

TABLE 3

Comparison Between 'EDZAM1901' and 'EDZAM1702'

| Characteristic | 'EDZAM1901' | 'EDZAM1702' |
|---|---|---|
| Abundance of foliage. | Less abundant. | More abundant. |
| Leaflet size. | Larger than 'EDZAM1702'. | Smaller than 'EDZAM1901'. |
| Leaflet shape. | Narrow obovate to oblanceolate. | Obovate to elliptic. |
| General coloration of the petiole. | Yellow-green; suffused and blotched brown. | Yellow-green. |
| General coloration of the foliage. | Darker shade of green compared to 'EDZAM1702'. | Lighter shade of green compared to 'EDZAM1901'. |

That which is claimed is:

1. A new and distinct variety of *Zamioculcas* plant named 'EDZAM1901', substantially as described and illustrated herein.

* * * * *